United States Patent [19]

Di Cosimo et al.

[11] Patent Number: 5,326,887

[45] Date of Patent: Jul. 5, 1994

[54] PROCESS FOR THE PREPARATION OF 1,4-DIOXANE-2,5-DIONES

[75] Inventors: Robert Di Cosimo, Wilmington, Del.; John R. Moran, Charleston, S.C.; Charles E. Nakamura, Claymont, Del.

[73] Assignee: E. I. Du Pont de Nemours and Company, Wilmington, Del.

[21] Appl. No.: 836,228

[22] Filed: Feb. 14, 1992

Related U.S. Application Data

[63] Continuation-in-part of Ser. No. 661,783, Feb. 27, 1991, abandoned.

[51] Int. Cl.$^5$ .............................................. C07D 323/04
[52] U.S. Cl. ..................................................... 549/274
[58] Field of Search ................................. 549/357, 274

[56] References Cited

U.S. PATENT DOCUMENTS

| | | | |
|---|---|---|---|
| 3,763,190 | 10/1973 | Ross et al. | 260/340.2 |
| 4,033,938 | 7/1977 | Augurt et al. | 260/78.3 |
| 4,727,163 | 2/1978 | Bellis | 549/274 |
| 4,835,293 | 5/1989 | Bhatia | 549/274 |
| 5,023,349 | 6/1989 | Bhatia | 549/274 |
| 5,043,458 | 8/1991 | Bhatia | 549/274 |
| 5,138,074 | 8/1992 | Bellis et al. | 549/274 |

FOREIGN PATENT DOCUMENTS 0339882  4/1989  European Pat. Off. .
92/05167  2/1992  World Int. Prop. O. .
92/05168  2/1992  World Int. Prop. O. .

OTHER PUBLICATIONS

J. Org. Chem., 38, 1602–5, 1973.
Zh. Prikl. Khim. (Leningrad), 53, 423–7, 1980.
A. C. Ibay, Army Inst. Dent. Res., Washington, DC; Report, Order No. Ad–A199413; Gov. Rep. Announce. Index (U.S.) 1989.
Chem. Express, 5, 149–52, 1990.
Angew. Chem., 91, 329–30, 1979.
Dahlmann et al., Chem. Abstracts, 111, No. 8, pp. 11, Oct. 26, 1988.
Raimo Alen et al., Acta Chem. Scand., Ser. B, 34, 633–6, 1980.
James K. Whitesell et al., Chem. Mater., 2, 248–54, 1990.
Synth. Commun., 17, 1919–28, 1987.
Org. Mass Spectrom., 2, 893–900, 1969.
Chem.–Ztg., 112, 125–7, 1988.
J. Am. Chem. Soc., 108, 5237–42, 1986.

*Primary Examiner*—C. Warren Ivy
*Assistant Examiner*—Raymond Covington

[57] ABSTRACT

This invention relates to a process for preparing 1,4-dioxane-2,5-diones comprising reacting an α-hydroxy acid oligomer or an ester of an α-hydroxy acid oligomer over a fixed bed catalyst system.

15 Claims, No Drawings

PROCESS FOR THE PREPARATION OF 1,4-DIOXANE-2,5-DIONES

This is a continuation-in-part of Ser. No. 07/661,783, filed on Feb. 27, 1991 now abandoned.

BACKGROUND OF THE INVENTION

1. Field of the Invention

This invention relates to a process for the preparation of 1,4-dioxane-2,5-diones which are useful for the preparation of degradable polymers.

2. Technical Background

The present invention provides a process for the preparation of 1,4-dioxane-2,5-diones, represented by Formula I, wherein each R is independently H or hydrocarbyl. These compounds are useful as precursors in the preparation of degradable polymers.

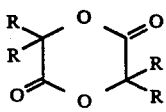

Compounds of Formula I are cyclic dimers of α-hydroxycarboxylic acids. In principle, two molecules of α-hydroxycarboxylic acids can condense to produce a compound of Formula I and two molecules of water. However, the direct formation of compounds of Formula I from α-hydroxycarboxylic acids is generally of limited preparative value, since it is most often the case that self-condensation of the α-hydroxycarboxylic acids forms a complex mixture of linear and cyclic oligomers resulting in poor yields. Acta Chem. Scand., Ser. B, 34, 633–6, 1980. This direct method affords poor yields of desired product even under dilute conditions where cyclization of a linear intermediate might be favored: 3,6-diphenyl-1,4-dioxane-2,5-dione was prepared from mandelic acid and a catalytic amount of p-toluene-sulphonic acid in refluxing benzene with water removal in only 11% yield with much oligomer formation. Chem. Mater., 2, 248–54, 1990. In what must be considered an exception to the rule, 3,3,6,6-tetraphenyl-1,4-dioxane-2,5-dione was similarly prepared from diphenylacetic acid in 93% yield. Synth. Commun., 17, 1919–28, 1987.

Compounds of Formula I have been more commonly prepared in a two-step reaction. In the first step, α-hydroxyacids are heated with the removal of water to form oligomers. In the second step, thermolysis of the oligomer is performed in the liquid phase in the presence of various catalysts at temperatures near 250° C. The compound of Formula I formed by this process is generally distilled from the reaction mixture as it is formed and is then crystallized from an appropriate solvent. Prior to crystallization, the crude product typically contains a significant amount of acidic impurities. This process suffers from excessive tar formation, low yields, and slow production rates. U.S. Pat. No. 4,835,293 discloses an improvement on this method whereby an inert gas is used to carry the product from the reaction mixture to a solvent system. U.S. Pat. No. 4,727,163 discloses an improvement whereby the thermolysis is performed on a block polymer comprising a thermally-stable polyether core with an α-hydroxyacid polymerized onto the core.

An alternative method for the production of compounds of Formula I involves the reaction of a carboxylic acid salt with a halide. EP 339,882 discloses that salts of 2-halopropionic acids, when heated at ca. 200° C. in organic solvents, form crude lactide from which lactide of high purity is obtained, after crystallization, in yields of approximately 15%. U.S. Pat. No. 3,763,190 discloses the preparation of 1,4-dioxane- 2,5-dione by heating sodium O-(chloroacetyl)glycolate at 125°–240° C. with sublimation of the products and purification by fractional vacuum sublimation at 0.03 torr and 25° C. Compounds of Formula I are also prepared by distillation of the sodium salts of the appropriate 2-bromocarboxylic acids. Org. Mass Spectrom., 2, 893–900, 1969.

Compounds of Formula I have also been obtained from methylarsino-substituted α-hydroxy carboxylate esters. Chem.-Ztg., 112, 125–7, 1988. Reaction of diphenylacetic acid in concentrated $H_2SO_4$ yields compounds of Formula I. J. Am. Chem. Soc., 108, 5237–42, 1986. Thermal or photochemical reaction of α-diazo ketones with molecular oxygen yields compounds of Formula I. J. Org. Chem., 38, 1602–5, 1973. Compounds of Formula I are obtained as a by-product in the manufacture of methacrylic acid via $H_2SO_4$ hydrolysis of methacrylamide. Zh. Prikl. Khim. (Leningrad), 53, 423–7, 1980.

The above methods have been used for the preparation of symmetrically 3,6-substituted 1,4-dioxane-2,5-diones (compounds of Formula I in which the substituents of carbon 3 are equivalent to the substituents at carbon 6). While unsymmetrically 3,6-substituted 1,4-dioxane-2,5-diones (compounds of Formula I in which at least one R group on the 3-carbon is different from at least one R group on the 6-carbon) can be obtained by the processes outlined above, the reactions would be expected to lead to a mixture of different 1,4-dioxane-2,5-diones. The separation of such a mixture would be difficult and would require extensive and costly purification procedures. For example, U.S. Pat. No. 4,033,938 discloses that thermolytic cracking of an oligomer prepared from glycolic acid and lactic acid provided a mixture of 1,4-dioxane-2,5-dione, 3-methyl-1,4-dioxane-2,5-dione and 3,6-dimethyl-1,4-dioxane-2,5-dione from which pure (>99%) 3-methyl-1,4-dioxane-2,5-dione was obtained only after repeated distillation.

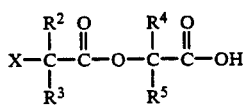

Unsymmetrically 3,6-substituted 1,4-dioxane-2,5-diones have been prepared from compounds of Formula II (X=Cl or Br; $R^2$, $R^3$, $R^4$, and $R^5$=H, alkyl or aralkyl). U.S. Pat. No. 4,033,938 discloses the production of 3-methyl-1,4-dioxane-2,5-dione and 3,3-dimethyl-1,4-dioxane-2,5-dione from O-(chloroacetyl) lactic acid and O-(chloroacetyl)-2-hydroxyisobutyric acid, respectively, in yields of approximately 25%. In each case, an arduous purification procedure was employed. The preparation of 3-methyl-1,4-dioxane-2,5-dione from O-(2-bromopropionyl)glycolic acid has been reported. A. C. Ibay (Army Inst. Dent. Res., Washington, DC); Report, Order No. AD-A199413; Gov. Rep. Announce. Index (U.S.) 1989, 89 (3). More recently, a reaction of dilute O-(chloroacetyl)lactic acid in dimethylformamide (2%, w/v) and a weak base was reported to give 3-methyl-1,4-dioxane-2,5-dione in yields as high as 87%. Chem. Express, 5, 149–52, 1990. A number of compounds of Formula II were prepared from α-bromocarboxylic acid chlorides and α-hydroxycarboxylic acids to give unsymmetrically 3,6-substituted 1,4-dioxane-2,5-diones in yields of 60–85% (Angew. Chem., 91, 329–30, 1979).

There exists a need for a process capable of producing 1,4-dioxane-2,5-diones cleanly, in high yield and without the necessity of extensive and costly purification procedures. In addition the process should provide unsymmetrically 3,6-substituted 1,4-dioxane-2,5-diones as well as symmetrically 3,6-substituted 1,4-dioxane-2,5-diones. It is the object of the present invention to provide such a process.

SUMMARY OF THE INVENTION

The present invention provides a process for the preparation of 1,4-dioxane-2,5-diones represented by Formula I comprising reacting an α-hydroxy acid oligomer or an ester of an α-hydroxy acid oligomer over a fixed-bed catalyst system, the reaction carried out at about 150° C. to about 350° C.

Also disclosed is a process for making optically active 1,4-dioxane-2,5-diones of the structure:

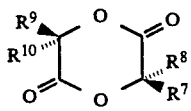

where:
a) $R^7$, $R^8$, $R^9$, and $R^{10}$ are independently H, unsubstituted straight chain alkyl, or unsubstituted branched chain alkyl; and
b) the structure contains at least one chiral center, by reacting an ester of an α-hydroxy acid dimer substrate of structure:

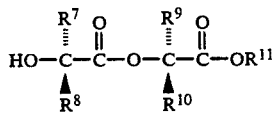

where $R^7$, $R^8$, $R^9$ and $R^{10}$ are defined above, $R^{11}$ is hydrocarbyl, and the structure contains at least one chiral center. That reaction carried out over a fixed bed catalyst, at about 150° C. to 250° C. The equivalent alcohol of $R^{11}$ has a pKa of less than 14.5. Optical purity of the product is in the range of 50–100% enantiometric excess.

DETAILED DESCRIPTION OF THE INVENTION

The present invention provides a novel route for the production of 1,4-dioxane-2,5-diones, represented by Formula I, optionally unsymmetrically substituted in the 3- and 6-positions. 1,4-Dioxane-2,5-diones are prepared by a vapor-phase pyrolyric ring closure of α-hydroxy acid oligomers or esters of α-hydroxy acid oligomers, represented by Formula III, over a fixed-bed catalyst system. The reaction is illustrated in Equation 1:

Equation 1

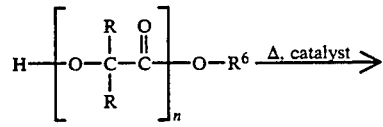

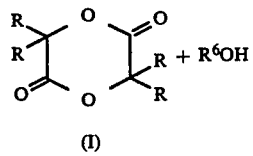

(I)

where each R and $R^6$ is independently hydrogen or hydrocarbyl and n=2, 3 or 4.

An important feature of the present invention is that each R group in the substrate represented by Formula III may be the same or may be different. This feature is exemplified in the compounds represented by Formulae IV and V which are typical substrates for the process of the present invention. Formula IV represents a compound of Formula III in which the R groups are different and n=2. Formula V represents a compound of Formula III in which the R groups are the same and n=4.

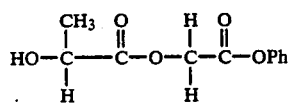

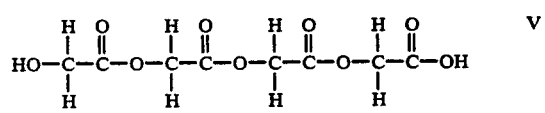

The substrates may be pure preparations or may be crude preparations (as described herein in Example 6). Esters of α-hydroxy acid dimers are preferred substrates. As the pKa of the equivalent alcohol of $R^6$ in the substrate is reduced, the reverse reaction of Equation 1 is also reduced. Preferred substrates are esters of α-hydroxy acid dimers where the equivalent alcohol of $R^6$ in Formula III has a pKa of less than 14.5. Most preferred substrates are those where the equivalent alcohol of $R^6$ is selected from a group including, but not limited to, 2-fluoroethanol, 2-chloroethanol, propargyl alcohol, 2,2,2-trifluoroethanol, 2,2,2,-trichloroethanol, and phenol.

The products provided by the process of the present invention are represented by Formula I. An important feature of the present invention is that each R group in the product represented by Formula I may be the same or may be different. This feature is exemplified in the compounds represented by Formulae VI and VII which are typical products provided by the process of the present invention. Formula VI represents a compound of Formula I in which the R groups are different. Formula VII represents a compound of Formula I in which the R groups are the same.

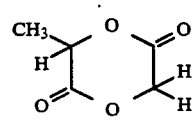

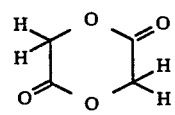

Optically active products can be provided by the process of the present invention. For example, an optically active compound of Formula IV may be used to prepare a compound of Formula VI which is enantiomerically pure (as described herein in Example 13). The reaction temperature is about 180° C. In contrast, under higher temperatures provided by the process of the present invention (e g about 300° C.) the same substrate provides a product which is essentially racemic, enantiomeric excess=7%, (as described herein in Example 14).

In carrying out the process of the present invention, a compound of Formula III, either neat or dissolved in an inert solvent, is fed over a fixed-bed catalyst at an appropriate temperature. The reaction effluent is collected in a trap optionally containing a suitable solvent. The pure compounds of Formula I are then obtained by methods commonly utilized by those skilled in the art.

If a solution of a compound of Formula III is used it is essential that the solvent be inert. It is anticipated that any inert solvent will be capable of withstanding temperatures up to 350° C. without degrading. Such solvents include, but are not limited to, tetrahydrofuran and toluene.

Preferred catalysts are aluminum oxides containing 0–18% silicon dioxide with surface areas of between 0.005 and 250 $m^2/g$, zirconium oxide, titanium (IV) oxide and molecular sieves. Most preferred catalysts have surface areas of between 0.04 and 35 $m^2/g$. Optionally, a preheating zone consisting of a bed of crushed quartz chips can be present.

This process is operable at, but not limited to, temperatures of between 150° and 350° C. The optimum temperature will, in part, depend upon the vapor pressure of the substrate. It is desirable that reaction take place at temperatures where substrates and products are present predominantly in the vapor-phase.

A stream of inert gas is used to maintain a contact time between substrate and catalyst of between 0.1 and 10 seconds. The short contact time serves to minimize the undesired reactions, for example, the addition of unreacted substrate to the labile 1,4-dioxane-2,5-dione product. It is anticipated that any inert gas would be suitable for use in this process, including nitrogen, helium and argon. The preferred inert gas is nitrogen.

The process of the present invention may be carried out at atmospheric, subatmospheric, or superatmospheric pressure.

The reaction effluent is collected in a trap optionally containing a suitable solvent cooled below 0° C. The list of solvents which may be used to collect the reaction effluent includes, but is not limited to, tetrahydrofuran and toluene.

The compounds of Formula I provided by this process may be further purified by methods known to those skilled in the art. For example, highly pure 1,4-dioxane-2,5-diones can be obtained by crystallization.

An important feature of this process is that it is performed in the vapor-phase. High dilution is obtained, favoring intramolecular cyclization of the substrate, without the necessity of using a large amount of solvent. The elimination of competing intermolecular reactions allows the use of α-hydroxy acid oligomers and their esters as substrates, which would otherwise be expected to form a mixture of monomers and linear and cyclic oligomeric products. Compounds of Formula I which are 3, 6-unsymmetrically substituted 1,4-dioxane-2,5-diones can be provided from compounds of Formula III where n=2 and at least one R group on one α-carbon is different from at least one R group on the other α-carbon. In this case, it is particularly important that intermolecular reactions be avoided since this can lead to the formation of unwanted cyclic homodimer products.

EXAMPLES

General Methods

A 69-cm length of 8-mm I.D./10 mm O.D. quartz tubing (Quartz Scientific, Inc.) was packed with 0.5–2.0 mL of catalyst using glass wool plugs which were optionally treated with Sigmacote ® (Sigma Chemical Co.). The catalysts were: 99.5+% α-$Al_2O_3$, S.A. 0.04 $m^2/g$, catalog #13-0750 from Strem Chemicals, Inc. (Catalyst A); 80.3% α-$Al_2O_3$ and 17.9% $SiO_2$, 25–35 $m^2/g$ catalog #SA 3232 from Norton Co. (Catalyst B); 86.1% α-$Al_2O_3$, 12.0% $SiO_2$, 0.005–0.040 $m^2/g$, catalog #SA 5218 from Norton Co. (Catalyst C); and crushed quartz (Catalyst D); zirconium oxide, catalog #86122 from Johnson Matthey Alfa Products (Catalyst E); titanium (IV) oxide, catalog #10897 from Alfa (Catalyst F); molecular sieves, type 3A, from Alfa (Catalyst G); and molecular selves, type 13X, from Alpha (Catalyst H). All catalysts were ground and screened to a mesh size of 28–35. The tubing was placed vertically in a Lindberg Model 55122-1 single zone tube furnace with a 30-cm heated zone, positioning the catalyst slightly above the middle of the heated zone. The top of the tubing was fitted with a T connecting the tubing to a Brooks Instruments mass flow controller calibrated for nitrogen at 1–120 mL/min and a syringe pump containing the substrate.

A solution of substrate in tetrahydrofuran was gravity fed into the fixed-bed reactor via a 22 gauge needle at a rate of between 0.5 and 1.5 mL/hr along with a stream of dry nitrogen at a rate of between 20–120 mL/min (STP). The reactor was maintained at a constant temperature of between 150° and 350° C. The reactor effluent was collected for 2–5 hr in a solvent trap containing tetrahydrofuran cooled on ice or dry ice. The contents of the trap were recovered along with any residue that collected on the lower portion of the tubing, the solvent was removed, and the residue was analyzed by $^1H$ NMR with $CDCl_3$ as solvent and tetramethylsilane as internal standard.

EXAMPLE 1

Synthesis of 3-Methyl-1,4-dioxane-2,5-dione by Pyrolysis of 2-Oxo-2-phenoxyethyl Lactate Experiment 1. A 10% solution (v/v in tetrahydrofuran) of 2-oxo-2-phenoxyethyl lactate was fed into a quartz tube containing 1 mL (1.56 g) of Catalyst A heated to 300° C. A silanized glass wool plug supported the catalyst. The feed rate was fixed at 1 mL/hr with a nitrogen stream of 29 mL/min (STP). Contact time (CT) and (weight feed/weight catalyst)/hr (WWH) were 0.94 s and 0.59 $hr^{-1}$ respectively. The effluent was collected in a solvent trap containing 10 mL of tetrahydrofuran cooled on ice. After 5 hr the feed was terminated, the bottom portion of the tube was washed with tetrahydrofuran, and the washing was added to the reactor effluent. The solvent was removed from the effluent by rotary evaporation under reduced pressure, and the residue was dissolved in ca. 2 mL of $CDCl_3$ containing 1% tetramethylsilane and 25 μL of tertbutylbenzene internal standard. $^1H$ NMR indicated the presence of 3-methyl-1,4-dioxane-2,5-dione: δ1.68 (d, J=6.9 Hz), δ4.84 (d, J=16.4 Hz), δ=4.92 (d, J=16.4 Hz), and δ4.97 (q, J=6.9 Hz); 2-oxo-2-phenoxyethyl lactate: δ1.50 (d, J=7.0 Hz), δ4.40–4.49 (m), δ4.88 (d, J=16.1 Hz), δ4.98 (d, J=16.2), and δ7.09–7.40 (phenyl); and phenol. Based on integration of the methyl peaks, 182 mg (1.40 mmol) of methylglycolide and 170 mg (0.76 mmol) of starting material were recovered for a conversion, selectivity, and mass balance of 71, 77 and 82%, respectively.

Experiments 2–22 were performed essentially as described in Experiment 1. The results are given in Table 1.

TABLE 1

| EXPT. | CATALYST (mL) | TEMP. (°C.) | CT (s) | WWH (1/hr) | CONVER. (%) | SELECT. (%) |
|---|---|---|---|---|---|---|
| 2 | A (1) | 300 | 1.35 | 0.60 | 66 | 85 |
| 3 | A (1) | 350 | 0.92 | 0.65 | 84 | 51 |
| 4 | A (2) | 280 | 1.40 | 0.29 | 72 | 72 |
| 5 | A (2) | 300 | 0.50 | 0.27 | 82 | 56 |
| 6 | A (2) | 300 | 0.97 | 0.28 | 86 | 63 |
| 7 | A (2) | 300 | 1.41 | 0.27 | 83 | 78 |
| 8 | A (2) | 300 | 1.41 | 0.27 | 71 | 68 |
| 9 | A (2) | 300 | 1.41 | 0.28 | 82 | 88 |
| 10 | A (2) | 300 | 1.89 | 0.14 | 73 | 79 |
| 11 | A (2) | 300 | 1.88 | 0.27 | 100 | 63 |
| 12 | A (2) | 300 | 1.88 | 0.27 | 84 | 71 |
| 13 | A (2) | 300 | 1.88 | 0.28 | 86 | 74 |
| 14 | A (2) | 300 | 1.83 | 0.43 | 87 | 69 |
| 15 | A (2) | 320 | 1.40 | 0.27 | 90 | 68 |
| 16 | D/A (2/2) | 300 | 3.76 | 0.18 | 87 | 76 |
| 17 | B (0.05) | 300 | 0.47 | 2.77 | 94 | 61 |
| 18 | B (1) | 300 | 0.94 | 1.39 | 100 | 54 |
| 19 | B (2) | 300 | 1.88 | 0.66 | 100 | 25 |
| 20 | D/B (1/0.5) | 300 | 1.41 | 0.72 | 98 | 56 |
| 21 | D (1) | 300 | 0.94 | 0.97 | 38 | 52 |
| 22 | C (2) | 300 | 1.88 | 0.36 | 63 | 71 |

EXAMPLE 2

Synthesis of 3-Methyl-1,4-dioxane-2,5-dione by Pyrolysis of 2-Methoxy-2-oxoethyl Lactate Solutions of 2-methoxy-2-oxoethyl lactate (10% v/v in tetrahydrofuran) were treated essentially as described above in Example 1, Experiment 1 to form 3-methyl-1,4-dioxane-2,5-dione. The results are given in Table 2.

TABLE 2

| EXPT. | CATALYST (mL) | TEMP. (°C.) | CT (s) | WWH (1/hr) | CONVER. (%) | SELECT. (%) |
|---|---|---|---|---|---|---|
| 1 | A (2) | 300 | 1.88 | 0.27 | 40 | 25 |
| 2 | D/B (1/0.5) | 300 | 1.41 | 0.72 | 98 | 7 |

EXAMPLE 3

Synthesis Of 3-Methyl-1,4-dioxene-2,5-dione by Pyrolysis of Methyl 2-(2-Hydroxy-1-oxoethoxy)propionate Solutions of methyl 2-(2-hydroxy-1-oxoethoxy)propionate (10% v/v in tetrahydrofuran) were treated essentially as described above in Example 1, Experiment to form 3-methyl-1,4-dioxane-2,5-dione. The results are given in Table 3.

TABLE 3

| EXPT. | CATALYST (mL) | TEMP. (°C.) | CT (s) | WWH (1/hr) | CONVER. (%) | SELECT. (%) |
|---|---|---|---|---|---|---|
| 1 | A (2) | 300 | 1.88 | 0.27 | 33 | 41 |
| 2 | D/B (1/0.5) | 300 | 1.41 | 0.78 | 93 | 35 |

EXAMPLE 4

Synthesis of 3-Phenyl-1,4-dioxane-2,5-dione by Pyrolysis of 2-Oxo-2-phenoxyethyl Mandelate Solutions of 2-oxo-2-phenoxyethyl mandelate (10% w/v in tetrahydrofuran) were treated essentially as described above in Example 1, Experiment 1. The amounts of 3-phenyl-1,4-dioxane-2,5-dione in the reactor effluent were determined by $^1$H NMR: δ4.84 (d, J=16.3 Hz), δ5.08 (d, J=16.2 Hz), δ6.14 (s), δ7.41 (phenyl). The results are given in Table 4.

TABLE 4

| EXPT. | CATALYST (mL) | TEMP. (°C.) | CT (s) | WWH (1/hr) | CONVER. (%) | SELECT. (%) |
|---|---|---|---|---|---|---|
| 1 | A (2) | 300 | 1.88 | 0.27 | 96 | 59 |
| 2 | D/B (1/0.5) | 300 | 1.41 | 0.71 | 98 | 45 |

EXAMPLE 5

Synthesis of 1,4-Dioxane-2,5-dione by Pyrolysis of 2-Methoxy-2-oxoethyl Glycolate Solutions of 2-methoxy-2-oxoethyl glycolate (10% v/v in tetrahydrofuran) were treated essentially as described above in Example 1, Experiment 1. 1,4-Dioxane-2,5-dione and 2-methoxy-2-oxoethyl glycolate were detected in the reactor effluent by $^1$H NMR: δ4.94 (s); and, δ3.79 (s), δ4.30 (s), and δ4.73 (s), respectively. The results are given in Table 5.

TABLE 5

| EXPT. | CATALYST (mL) | TEMP. (°C.) | CT (s) | WWH (1/hr) | CONVER. (%) | SELECT. (%) |
|---|---|---|---|---|---|---|
| 1 | A (2) | 300 | 1.88 | 0.27 | 41 | 33 |
| 2 | D/B (1/0.5) | 300 | 1.41 | 0.75 | 94 | 22 |

EXAMPLE 6

Synthesis of 1,4-Dioxane-2,5-dione by Pyrolysis of Glycolic Acid Preparations

Solutions of glycolic acid preparations (10% w/v in tetrahydrofuran) were treated essentially as described above in Example 1, Experiment 1. In Experiments 1 and 2, the substrate solution was prepared from 99% glycolic acid (Aldrich Chemical Company, Inc., catalog number 12,473-7). In Experiments 3, 4, and 5, aliquots of 99% glycolic acid were heated in open flasks at ca. 110° C. until weight losses of 4.8, 8.8 and 12.0%, respectively, occurred. The relative amounts of monomer, dimer, trimer and tetramer in the treated glycolic acid preparations were quantitated by gas chromatography on samples derivatized with N-methyl-N-(trimethylsilyl)-trifluoroacetamide. The peak integrations (FID detection) are given in Table 6. The amount of 1,4-dioxane-2,5-dione in the reactor effluent was determined by 1H NMR (tetrahydrofuran-d8, TMS): δ4.94 (s). The results are summarized in Table 7.

TABLE 6

| EXPERIMENT | % OF TOTAL GC INTEGRATION | | | |
|---|---|---|---|---|
| | (monomer) | (dimer) | (trimer) | (tetramer) |
| 3 | 54 | 28 | 13 | 6 |
| 4 | 51 | 28 | 14 | 7 |
| 5 | 44 | 28 | 17 | 11 |

TABLE 7

| EXPT. | CATA-LYST (mL) | TEMP. (°C.) | CT (s) | WWH (1/hr) | CON-VER. (%) | SELECT. (%) |
|---|---|---|---|---|---|---|
| 1 | A (2) | 300 | 1.41 | 0.26 | 66 | 11 |
| 2 | D/B (1/0.5) | 300 | 10.6 | 0.82 | 100 | 2 |
| 3 | A (2) | 300 | 1.41 | 0.27 | 84 | 17 |
| 4 | A (2) | 300 | 1.41 | 0.28 | 84 | 22 |
| 5 | A (2) | 300 | 1.41 | 0.27 | 89 | 19 |

EXAMPLE 7

Synthesis of 3-Butyl-1,4-dioxane-2,5-dione by Pyrolysis of 2-oxo-2-phenoxyethyl 2-Hydroxycaproate Experiments 1-3. Solutions of 2-oxo-2-phenoxyethyl 2-hydroxycaproate (10% w/v in tetrahydrofuran) were treated essentially as described above in Example 1, Experiment 1, except that the quartz tube diameter, feed rate and nitrogen stream were increased by approximately a factor of four. 3-Butyl-1,4-dioxane-2,5-dione was detected by NMR and the results are given in Table 8.

TABLE 8

| EXPT. | CATA-LYST (mL) | TEMP. (°C.) | CT (s) | WWH (1/hr) | CON-VER. (%) | SELECT. (%) |
|---|---|---|---|---|---|---|
| 1 | D/A (2/8) | 210 | 2.71 | 0.22 | 47 | 100 |
| 2 | D/A (2/8) | 300 | 2.72 | 0.22 | 100 | 90 |
| 3 | D/B (2/2) | 300 | 0.94 | 1.02 | 100 | 95 |

Experiment 4. 2-Oxo-2-phenoxyethyl 2-hydroxycaproate (240 mL of a 10% w/v solution in tetrahydrofuran at 10 mL/hr) and nitrogen (300 mL/min) were passed through a 23-mm I.D. quartz tube containing 5 mL of coarsely crushed quartz on top of 15 mL of Catalyst A heated to 300° C. Contact time and WWH were 1.83 s and 0.28 hr$^{-1}$ respectively. Conversion and selectivity, determined by integration of NMR spectra, were 100% and 80%, respectively. The column effluent was rotovaped, phenol was removed by distillation under reduced pressure, and a fraction which was predominantly product was obtained by distillation (13.2 g, 98°-110° C./0.1 mm Hg). Crystallization from 30 mL of dry isopropanol gave 8.28 g (48.1 mmol) 3-butyl-1,4-dioxane-2,5-dione. mp 37°-39° C. $^1$H NMR (300 MHz, CDCl$_3$): δ0.94 (t, 3H, J=7.2 Hz), δ1.4-1.6 (m, 4H), δ1.9-2.15 (m, 2H), δ4.89 (d, 1H, J=16.5 Hz), ca δ4.92 (m, 1H), and δ4.91 (d, 1H, J=16.5 Hz). $^{13}$C NMR: (75 MHz, CDCl$_3$): 13.6, 22.0, 26.4, 30.5, 65.3, 75.6, 164.4, and 165.7. HRMS: calcd for C$_8$H$_{12}$O$_4$=172.0735, found 172.0757.

EXAMPLE 8

Synthesis of 1,4-Dioxaspiro [5.5]undecane-2,5-dione by Pyrolysis of 2-Oxo-2-phenoxyethyl 1-Hydroxy-1-cyclohexanecarboxylate Experiments 1-3. Solutions of 2-oxo-2-phenoxyethyl 1-hydroxy-1-cyclohexanecarboxylate (10% w/v in tetrahydrofuran) were treated essentially as described above in Example 7, Experiments 1-3 to form 1,4-dioxaspiro[5.5]undecane-2,5-dione. The results are given in Table 9. Due to the complexity of the NMR spectra of these reactions, conversion and selectivity data are maximum values.

TABLE 9

| EXPT. | CATA-LYST (mL) | TEMP. (°C.) | CT (s) | WWH (1/hr) | CON-VER. (%) | SELECT. (%) |
|---|---|---|---|---|---|---|
| 1 | D/A (2/8) | 210 | 2.71 | 0.23 | 69 | 22 |
| 2 | D/A (2/8) | 300 | 2.72 | 0.23 | 87 | 61 |
| 3 | D/B (2/2) | 210 | 1.12 | 1.08 | 100 | 71 |

Experiment 4. 2-Oxo-2-phenoxyethyl 1-hydroxy-1-cyclohexanecarboxylate (130 mL of a 10% w/v solution in tetrahydrofuran at 10 mL/hr) and nitrogen (230 mL/min) were passed through a 23-mm I.D. quartz tube containing 4 mL of coarsely crushed quartz on top of 4 mL of Catalyst B (1/16" pellets) heated to 210° C. Contact time and WWH were 1.10 s and 1.22 hr$^{-1}$, respectively. The column effluent was rotovaped, phenol was removed by distillation under reduced pressure to give 7.55 g of a yellow oil. Crystallization from anhydrous isopropanol/petroleum ether (bp 35°-60° C.) gave 4.11 g (22.3 mmol) 1,4-dioxaspiro[5.5]undecane-2,5-dione. mp 67°-68° C. $^1$H NMR (300 MHz, CDCl$_3$): δ1.40 (m, 1H), δ1.66-1.80 (m, 5H), δ1.97-2.06 (m, 4H), and d 4.95 (s, 2H). $^{13}$C NMR (75 MHz, CDCl$_3$): 20.1, 20.3, 24.2, 33.2, 33.4, 65.3, 81.0, 163.8, and 167.4. HRMS: calcd for C$_9$H$_{12}$O$_4$=184.0735, found 184.0744.

EXAMPLE 9

Synthesis of 3-Methyl-3-phenyl-1,4-dioxane-2,5-dione by Pyrolysis of 2-Oxo-2-phenoxyethyl Atrolactate Experiments 1-4. Solutions of 2-oxo-2-phenoxyethyl atrolactate (10% w/v in tetrahydrofuran) were treated essentially as described above in Example 7, Experiments 1-3 to form 3-methyl-3-phenyl-1,4-dioxane-2,5-dione The results are given in Table 10.

TABLE 10

| EXPT. | CATA-LYST (mL) | TEMP. (°C.) | CT (s) | WWH (1/hr) | CON-VER. (%) | SELECT. (%) |
|---|---|---|---|---|---|---|
| 1 | D/A (2/8) | 210 | 2.71 | 0.22 | 39 | 100 |
| 2 | D/A (2/8) | 300 | 2.72 | 0.23 | 98 | 85 |
| 3 | D/B (2/2) | 210 | 1.12 | 0.93 | 100 | 74 |
| 4 | D/B (2/2) | 300 | 0.94 | 1.03 | 100 | 20 |

Experiment 5. 2-Oxo-2-phenoxyethyl atrolactate (45.5 g, 152 mmol) was reacted as described in Example 7, Experiment 4. Midway through the reaction, the feed was interrupted and the catalyst was regenerated by heating at 400° C. for 30 min under a flow of compressed air. Contact time and WWH were 1.83 s and 0.28 hr$^{-1}$ respectively. Conversion and selectivity were 100% and 78%, respectively. After the solvent was rotovaped, two crystallizations from anhydrous isopropanol gave 17.7 g (85.9 mmol) of 3-methyl-3-phenyl-1,4-dioxane-2,5-dione. mp 90°–91° C. $^1$H NMR (300 MHz, CDCl$_3$): δ1.91 (s, 3H), δ4.36 (d, 1H, J=16.6 Hz), δ4.74 (d, 1H, J=16.6 Hz), and δ7.4–7.5 (phenyl, 5 H). $^{13}$C NMR (75 MHz, CDCl$_3$): 28.0, 66.1, 83.8, 123.9, 129.6, 129.7, 137.2, 164.8, and 166.2. HRMS calcd for C$_{11}$H$_{10}$O$_4$=206.0579, found 206.0587.

EXAMPLE 10

Synthesis of 3-Phenyl-1,4-dioxane-2,5-dione by Pyrolysis of 2-Oxo-2-phenoxyethyl Mandelate 2-Oxo-2-phenoxyethyl mandelate was prepared from (S)-(+)-tetramethyammonium mandelate and phenylbromoacetate. mp 123°–124.5° C. $^1$H NMR (300 MHz, CDCl$_3$): δ3.39 (d, 1H, J=5.4 Hz), δ4.86 (d, 1H, J=16.0 Hz), δ4.92 (d, 1H, J=16.0 Hz), δ5.34 (d, 1H, J =5.3 Hz), and δ7.0–7.5 (phenyl, 5H). $^{13}$C NMR (75 MHz, CDCl$_3$): 61.7, 73.2, 121.1, 126.2, 126.9, 128.6, 129.5, 137.7, 150.1, 165.3, and 172.9. HRMS calcd for C$_{16}$H$_{13}$O$_5$TMS—CH$_3$=343.1001, found 343.1076.

Experiments 1–4. Solutions of 2-oxo-2-phenoxyethyl mandelate (10% w/v in tetrahydrofuran) were treated essentially as described above in Example 1, Experiment 1. The column effluents were rotovaped, the resulting solid-oil mixture was washed with ethyl ether, and the solid was recovered by filtration and identified as 3-phenyl-1,4-dioxane-2,5-dione by GC. No material was recovered from the column effluents in identical experiments performed at 150° and 180° C., presumably due to the absence of volatilization. The results are given in Table 11.

TABLE 11

| EXPT. | CATALYST (mL) | TEMP. (°C.) | CT (s) | WWH (1/hr) | CONVER. (%) | SELECT. (%) |
|---|---|---|---|---|---|---|
| 1 | D/A (0.5/2) | 210 | 2.79 | 2.14 | 97 | 64 |
| 2 | D/A (0.5/2) | 240 | 2.64 | 2.26 | 94 | 64 |
| 3 | D/A (0.5/2) | 270 | 2.49 | 2.06 | 97 | 54 |
| 4 | D/A (0.5/2) | 300 | 2.35 | 2.26 | 95 | 40 |

Experiment 5. 2-Oxo-2-phenoxyethyl mandelate (240 mL of a 10% w/v solution in tetrahydrofuran at 10 mL/hr) and nitrogen (300 mL/hr) were passed through a 23-mm I.D. quartz tube containing 5 mL of coarsely crushed quartz on top of 10 mL of Catalyst A heated to 300° C. Contact time and WWH were 1.37 s and 0.38 hr$^{-1}$, respectively. Conversion and selectivity were 100% and 52%, respectively. A portion of the column effluent was rotovaped, the resulting solid-oil mixture was washed with ethyl ether, and the solid 3-phenyl-1,4-dioxane-2,5-dione was recovered by filtration. mp 130°–132° C. (crystallized from anhydrous isopropanol). $^1$H NMR (300 MHz, CDCl$_3$): δ4.84 (d, 1H, J=16.3 Hz), δ5.08 (d, 1H, J=16.2 Hz), δ6 14 (s, 1H), and δ7.4–7.45 (phenyl, 5H). $^{13}$C NMR (75 MHz, CDCl$_3$): 65.2, 77.5, 125.7, 129.5, 130.0, 131.1, 163.9, and 164.0. HRMS calcd for C$_{10}$H$_8$O$_4$=192.0422, found 192.0414.

EXAMPLE 11

Synthesis of 3-Phenylmethyl-1,4-dioxane-2,5-dione Pyrolysis of 2-Oxo-2-phenoxyethyl 3-Phenyllactate (S)-(−)-Tetramethylammonium 3-phenyllactate and phenyl bromoacetate were condensed to give 2-oxo-2-phenoxyethyl 3-phenyllactate. mp 98°–99° C. $^1$H NMR (300 MHz, CDCl$_3$): δ3.02 (dd, 1H, J=7.5 and 14.1 Hz), δ3.24 (dd, 1H, J=4.3 and 14.1 Hz), δ4.58 (dd, 1H, J=4.3 and 7.5 Hz), δ4.88 (d, 1H, J=16.1 Hz), δ4.98 (d, 1H, J=16.1 Hz), and δ7.1–7.45 (phenyl, 10 H). $^{13}$C NMR (75 MHz, CDCl$_3$): 40.5, 61.3, 71.4, 121.2, 126.3, 126.9, 128.4, 129.5, 136.3, 150.2, 165.6, and 173.4. HRMS calcd for C$_{17}$H$_{15}$O$_5$TMS—CH$_3$=357.1158, found 357.1163.

Experiments 1–7. Solutions of 2-oxo-2-phenoxyethyl 3-phenyllactate (10% w/v in tetrahydrofuran) were treated essentially as described above in Example 7, Experiments 1–3 to form 3-phenylmethyl-1,4-dioxane-2,5-dione. The results are given in Table 12.

TABLE 12

| EXPT. | CATALYST (mL) | TEMP. (°C.) | CT (s) | WWH (1/hr) | CONVER. (%) | SELECT. (%) |
|---|---|---|---|---|---|---|
| 1 | D/A (2/4) | 210 | 1.62 | 0.40 | 97 | 68 |
| 2 | D/A (2/6) | 210 | 2.17 | 0.28 | 100 | 70 |
| 3 | D/A (2/8) | 210 | 2.71 | 0.22 | 100 | 75 |
| 4 | D/A (2/1) | 230 | 0.79 | 0.22 | 98 | 73 |
| 5 | D/A (2/1) | 250 | 0.75 | 0.23 | 99 | 73 |
| 6 | D/B (2/1) | 180 | 0.81 | 1.35 | 97 | 31 |
| 7 | D/B (2/1) | 210 | 0.81 | 1.38 | 97 | 56 |

Experiment 8. 2-oxo-2-phenoxyethyl 3-phenyllactate (240 mL of a 10% w/v solution in tetrahydrofuran at 10 mL/hr) and nitrogen (240 mL/min) were passed through a 23-mm I.D. quartz tube containing 4 mL of coarsely crushed quartz on top of 4 mL of Catalyst A heated to 250° C. Contact time and WWH were 0.98 s and 0.77 hr$^{-1}$, respectively. The column effluent was rotovaped, phenol was removed by distillation under reduced pressure to give crude product. Two crystallizations from anhydrous isopropanol gave 7.53 g (36.5 mmol) of 3-phenylmethyl-1,4-dioxane-2,5-dione. mp 64°–65° C. $^1$H NMR (300 MHz, CDCl$_3$): δ3.28 (dd, 1H, J=5.7 and 14.6 Hz), δ3.37 (dd, 1H, J=4.6 and 14.7 Hz), δ3.89 (d, 1H, J=16.8 Hz), d 4.60 (d, 1H, J=16.8 Hz), δ5.17 (dd, 1H, J=4.6 and 5.7 Hz), and δ7.2–7.4 (phenyl, 5H). $^{13}$C NMR (75 MHz, CDCl$_3$): 38.2, 65.0, 76.9, 128.1, 129.2, 130.1, 134.1, 163.4, and 165.1. HRMS calcd for C$_{11}$H$_{10}$O$_4$=206.0579, found 206.0574.

EXAMPLE 12

Synthesis of 3-Methyl-1,4-dioxane-2,5-dione by Pyrolysis of (S)-(−)-2-Oxo-2-phenoxyethyl Lactate (S)-(−)-2-Oxo-2-phenoxyethyl lactate was prepared from (S)-(−)-tetramethylammonium lactate and phenyl bromoacetate. An analytical sample of the oil was prepared by chromatography on silica gel (ethyl acetate/hexane). [α]$^{25}_D$= −12.1°±0.4 (c=1.19, CHCl$_3$). $^1$H NMR (300 MHz, CDCl$_3$): δ1.50 (d, 3H, J=7.0), δ3.12 (d, 1H, J=5.3), δ4.40–4.49 (m, 1H), δ4.87 (d, 1H, J=16.1), δ4.99 (d, 1H, J=16.2), δ7.09–7.40 (5H, phenyl). $^{13}$C NMR (75 MHz, CDCl$_3$): 20.5, 61.4, 67.1, 121.3, 126.5, 129.7, 15.03, 165.9, and 175.1. HRMS calcd for C$_{10}$H$_8$O$_5$TMS (M—CH$_3$) 281.0845, obsd 281.0856.

Experiments 1-6. Solutions of (S)-(—)-2-Oxo-2-phenoxyethyl lactate (10% w/v in tetrahydrofuran) were treated essentially as described above in Example 1, Experiment 1 to give 3-methyl-1,4-dioxane-2,5-dione. The results are given in Table 13. Optical rotation was not determined.

Experiments 7-10. Solutions of (S)-(—)-2-Oxo-2-phenoxyethyl lactate (10% w/v in tetrahydrofuran) were treated essentially as described above in Example 7, Experiments 1-13 to give 3-methyl-1,4-dioxane-1,5-dione. The results are given in Table 13 Optical rotation was not determined.

TABLE 13

| EXPT. | CATA-LYST (mL) | TEMP. (°C.) | CT (s) | WWH (1/hr) | CON-VER. (%) | SELECT. (%) |
|---|---|---|---|---|---|---|
| 1 | D/B (0.5/0.5) | 150 | 1.28 | 1.38 | 100 | 60 |
| 2 | D/B (0.5/0.5) | 180 | 1.20 | 1.27 | 100 | 81 |
| 3 | D/B (0.5/0.5) | 210 | 1.16 | 1.23 | 96 | 83 |
| 4 | D/B (0.5/0.5) | 240 | 1.06 | 1.28 | 96 | 81 |
| 5 | D/B (0.5/0.5) | 270 | 1.00 | 1.18 | 94 | 69 |
| 6 | D/B (0.5/0.5) | 300 | 0.94 | 1.20 | 97 | 70 |
| 7 | D/E (2/8) | 180 | 2.89 | 0.16 | 100 | ca 71 |
| 8 | D/F (2/8) | 180 | 2.89 | 0.39 | 100 | 43 |
| 9 | D/G (2/8) | 180 | 2.89 | 0.50 | 100 | 70 |
| 10 | D/H (2/8) | 180 | 2.89 | 0.53 | 100 | 13 |

EXAMPLE 13

Synthesis Of (S)-(—)-3-Methyl-1,4-dioxane-2,5-dione by Pyrolysis Of (S)-(—)-2-Oxo-2-phenoxyethyl Lactate at 180° C.

Experiment 1. (S)-(—)-2-Oxo-2-phenoxyethyl lactate (240 mL of a 10% w/v solution in tetrahydrofuran at 10 mL/hr) and nitrogen (300 mL/hr) were passed through a 23-mm I.D. quartz tube containing 5 mL of coarsely crushed quartz on top of 5 mL of Catalyst B (1/16" spheres) heated to 180° C. Contact time and WWH were 0.92 s and 0 97 hr$^{-1}$ respectively. Conversion and selectivity were 95% and 72%, respectively. The column effluent was fractionated by distillation and 10.0 g of an oil (predominantly product as determined by NMR) was recovered at 68°-110° C./0.5-5 mm Hg. Addition of 100 mL ethyl ether caused the precipitation of 6.03 g of a white solid. An analytical sample of (S)-(—)-3-methyl-1,4-dioxane-2,5-dione, prepared by crystallization from anhydrous isopropanol, gave: $[\alpha]^{25}_D = -210° \pm 0.8$ (c=1.19, CHCl$_3$) and $[\alpha]^{25}_D = -254° \pm 0.9$ (c=1.14, benzene). [Lit. $[\alpha]^{25}_D = -245° \pm 01.0$ (c=0.988, benzene), Augurt et al., U.S. Pat. No. 4,033,938.]

Experiment 2. Five consecutive reactions of 240 mL 10% (w/v) (S)-(—)-2-oxo-2-phenoxyethyl lactate in tetrahydrofuran were performed on a 23-mm I.D. quartz tube containing 5 mL of coarsely crushed quartz on top of 7.5 mL of Catalyst B (1/16" spheres) heated to 180° C. Feed flow rate and nitrogen flow rate were 10 mL/hr and 300 mL/min, respectively. Contact time and WWH were 1.45 s and 0 84 hr$^{-1}$ respectively. After the third reaction, the catalyst was regenerated by heating at 400° C. for 30 min under a flow of compressed air. Conversion and selectivity were determined for each reaction—the average values were 91% and 90% respectively. Crude product from each reaction, obtained by distillation under reduced pressure, was combined and redistilled to give the following fractions:

| FRACTION NUMBER | bp (°C.)/ 0.3 mm Hg | WEIGHT (g) | $[\alpha]_D^{25}$ (c ≈ 1, CDCl$_3$) |
|---|---|---|---|
| 1 | 62-84 | 3.46 | −96.9° ± 0.4 |
| 2 | 84 | 7.35 | −152.9° ± 0.4 |
| 3 | 87 | 14.48 | −191.2° ± 0.4 |
| 4 | 95 | 19.58 | −194.2° ± 0.4 |

An analytical sample of (S)-(—)-3-methyl-1,4-dioxane-2,5-dione, prepared from Fraction 3 by crystallization from anhydrous isopropanol, gave $[\alpha]^{25}_D = -219° \pm 0.9$ (c=1.15, CHCl$_3$) and $[\alpha]^{25}_D = -261° \pm 1.0$ (c=1.05, benzene).

EXAMPLE 14

Synthesis of 3-Methyl-1,4-dioxane-2,5-dione by Pyrolysis of (S)-(—)-2-Oxo-2-phenoxyethyl Lactate at 300° C.

(S)-(—)-2-Oxo-2-phenoxyethyl lactate was treated exactly as described in Example 13 except that the temperature was 300° C. Contact time and WWH were 0.92 s and 0.95 hr$^{-1}$, respectively. Conversion and selectivity were 100% and 77%, respectively. The column effluent was fractionated by distillation and 12.46 g of an oil (predominantly product as determined by NMR) was recovered at 68°-110° C./0.5-5 mm Hg. Addition of 20 mL of ethyl ether caused the precipitation of 10.2 g of a waxy solid and crystallization from toluene provided 5.61 g of product (pure as determined by NMR) as a waxy solid. Recrystallization of 1.08 g of this material from anhydrous isopropanol gave 0.42 g of product as a white, powdery solid. $[\alpha]^{25}_D = -15.3° \pm 0.8$ (C=1.02, CHCl$_3$).

Although preferred embodiments of the invention have been described hereinabove, it is to be understood that there is no intention to limit the invention to the precise constructions herein disclosed and it is to be further understood that the right is reserved to all changes coming within the scope of the invention as defined by the appended claims.

What is claimed is:

1. A process for making 1,4-dioxane-2,5-diones of the structure:

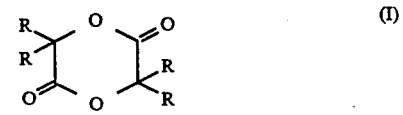

(I)

wherein each R is independently H or hydrocarbyl, optionally substituted with a halogen, by reacting an ester of an α-hydroxy acid dimer substrate of structure:

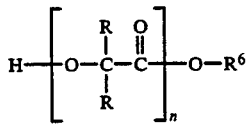

wherein each R is independently hydrogen on hydrocarbyl, optionally substituted with a halogen, and $R^6$ is hydrocarbyl, optionally substituted with a halogen, and n=2, over a fixed bed catalyst, the process carried out at about 150° C. to about 350° C., wherein the reactants are in the vapor phase, followed by collection of the effluent product and wherein the equivalent alcohol of $R^6$ has a pKa of less than 14.5.

2. The process of claim 1 wherein the equivalent alcohol of $R^6$ is selected from a group consisting of 2-fluoroethanol, 2-chloroethanol, propargyl alcohol, 2,2,2-trifluoroethanol, 2,2,2-trichloroethanol and phenol.

3. The process of claim 1 wherein the substrate is first dissolved in an inert solvent, prior to heating.

4. The process of claim 3 wherein the solvent is capable of withstanding temperatures up to 350° C. without solvent degradation.

5. The process of claim 4 wherein the solvent is selected from tetrahydrofuran and toluene.

6. The process of claim 1 wherein the catalyst is aluminum oxide.

7. The process of claim 6 wherein the catalyst additionally contains up to 18% silicon dioxide.

8. The process of claim 1 wherein the contact time between substrate and catalyst is 0.1 to 10 seconds.

9. The process of claim 8 wherein a stream of inert gas is added to the reaction mixture.

10. The process of claim 9 wherein the inert gas is selected from the group consisting of nitrogen, helium and argon.

11. The process of claim 10 wherein the inert gas is nitrogen.

12. A process for making optically active 1,4-dioxane-2,5-diones of the structure:

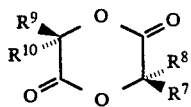

where:

a) $R^7$, $R^8$, $R^9$, and $R^{10}$ are independently H, unsubstituted straight chain alkyl, or unsubstituted branched chain alkyl; and b) the structure contains at least one chiral center, by reacting an ester of an α-hydroxy acid dimer substrate of structure:

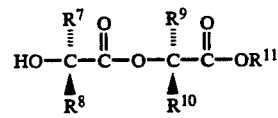

where $R^7$, $R^8$, $R^9$, and $R^{10}$ are defined above, $R^{11}$ is hydrocarbyl, optionally substituted with a halogen, and the structure contains at least one chiral center, the reaction carried out over a fixed bed catalyst, at about 150° C. to 250° C., wherein the reactants are in the vapor phase and wherein the equivalent alcohol of $R^{11}$ has a pKa of less than 14.5.

13. The process of claim 1 wherein the catalyst is selected from zirconium oxide, titanium (IV) oxide, and molecular sieves type 3A and molecular sieves type 13X.

14. The process of claim 1 for making 1,4-dioxane 2,5-diones of the structure:

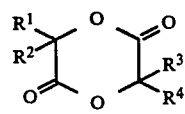

wherein the substrate is a composition represented by the following Formula A:

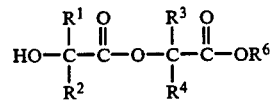

wherein:

$R^1$, $R^2$, $R^3$, and $R^4$ are each independently selected from H and hydrocarbyl and wherein $R^1$ and $R^2$ are not the same as $R^3$ and $R^4$ and wherein $R^6$ is hydrocarbyl, optionally substituted with a halogen.

15. The process of claim 14 wherein $R^1$, $R^2$, $R^3$, and $R^4$ are selected from the group consisting of hydrogen, alkyl, aryl, alkaryl, and aralkyl and $R^6$ is selected from the group consisting of haloalkyl, and aryl.

* * * * *